(12) United States Patent
Buskop

(10) Patent No.: US 7,603,078 B2
(45) Date of Patent: Oct. 13, 2009

(54) SKI GOGGLES WITH DIGITAL MUSIC PLAYER

(76) Inventor: Wendy K B Buskop, 2241 Del Monte Dr., Houston, TX (US) 77019

( * ) Notice: Subject to any disclaimer, the term of this patent is extended or adjusted under 35 U.S.C. 154(b) by 669 days.

(21) Appl. No.: 10/907,699

(22) Filed: Apr. 12, 2005

(65) Prior Publication Data

US 2006/0225188 A1    Oct. 12, 2006

(51) Int. Cl.
*H04H 40/00* (2008.01)
(52) U.S. Cl. .................... 455/3.06; 455/3.01; 351/158; 381/327

(58) Field of Classification Search ............... 455/3.01, 455/3.06, 7–10, 14–25; 351/158; 381/327; 370/315
See application file for complete search history.

(56) References Cited

U.S. PATENT DOCUMENTS 6,325,507 B1    12/2001  Jannard
7,500,747 B2 *   3/2009  Howell et al. ............... 351/158

FOREIGN PATENT DOCUMENTS

JP            02166844 A  *  6/1990

* cited by examiner

*Primary Examiner*—Raymond S Dean
(74) *Attorney, Agent, or Firm*—Buskop Law Group, PC

(57) ABSTRACT

A ski goggle with a digital sound playing system, a ski theme park and a ski slope having specially designed music transmitted over each slope.

3 Claims, 3 Drawing Sheets

SKI GOGGLES WITH DIGITAL MUSIC PLAYER

FIELD OF INVENTION

The present embodiments relate generally to ski goggles for adults or children with an integrated digital music player and earphones and a wireless connection to members of an audience watching downhill racers.

BACKGROUND

The present invention relates to ski goggles which are single lens or double lens and are used on adults or children.

Skiers who are training for the Olympics and for racing have used music broadcast over loudspeakers to learn rhythm to traverse moguls quickly. The broadcast music is land based typically at the bottom of the mogul field and is very loud, disturbing everyone around the race course. Typically, the announcer can not even speak or announce the names of skiers over the loud music needed for the racers.

A need has existed for a ski goggle that links to a broadcast system so the individual skier can hear the music, select audience members can hear the music, and broadcast of the music is optional to the slopes to stop the noise on the adjacent slopes during a race.

The noise is known to distract skiers, particularly children, who do not pay attention to their skiing, and crash into people breaking arms and causing damage. Such accidents have happened at Park City Ski Resort in Park City Utah, and at Killington Ski area in Killington Vt., and should be stopped, and not repeated.

A need has existed for a ski goggle that can hold numerous files of digital music such as an IPOD for use with the training of ski racers.

The present invention meets these needs.

BRIEF DESCRIPTION OF THE DRAWINGS

The detailed description will be better understood in conjunction with the accompanying drawings as follows.

The present embodiments are detailed below with reference to the listed Figures.

DETAILED DESCRIPTION OF THE PREFERRED EMBODIMENTS

Before explaining the present embodiments in detail, it is to be understood that the embodiments are not limited to the particular embodiments and that it can be practiced or carried out in various ways.

Figure 1:
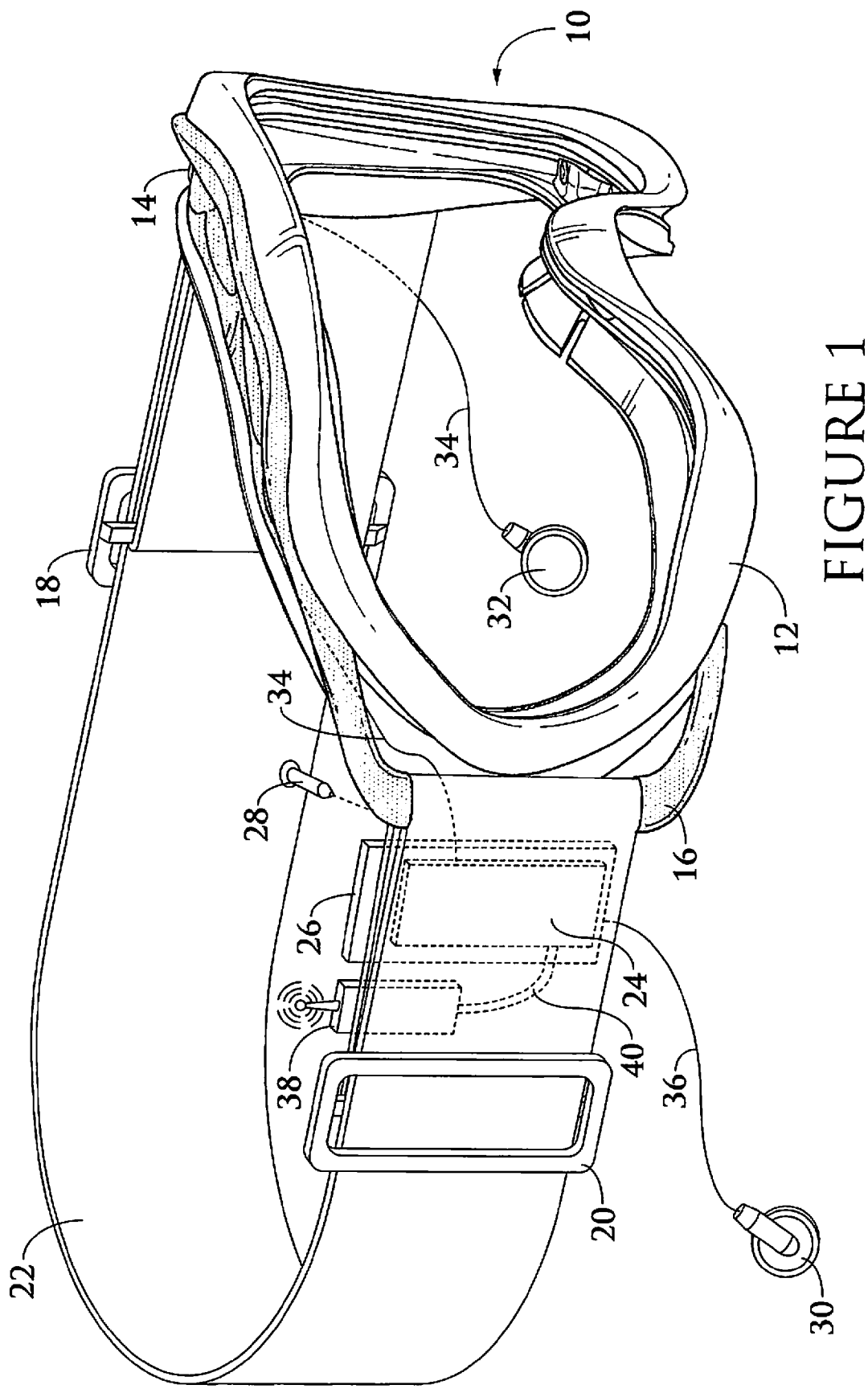
FIG. 1 depicts a perspective view of the ski goggle with digital receiver and player embodiment.
Figure 2:
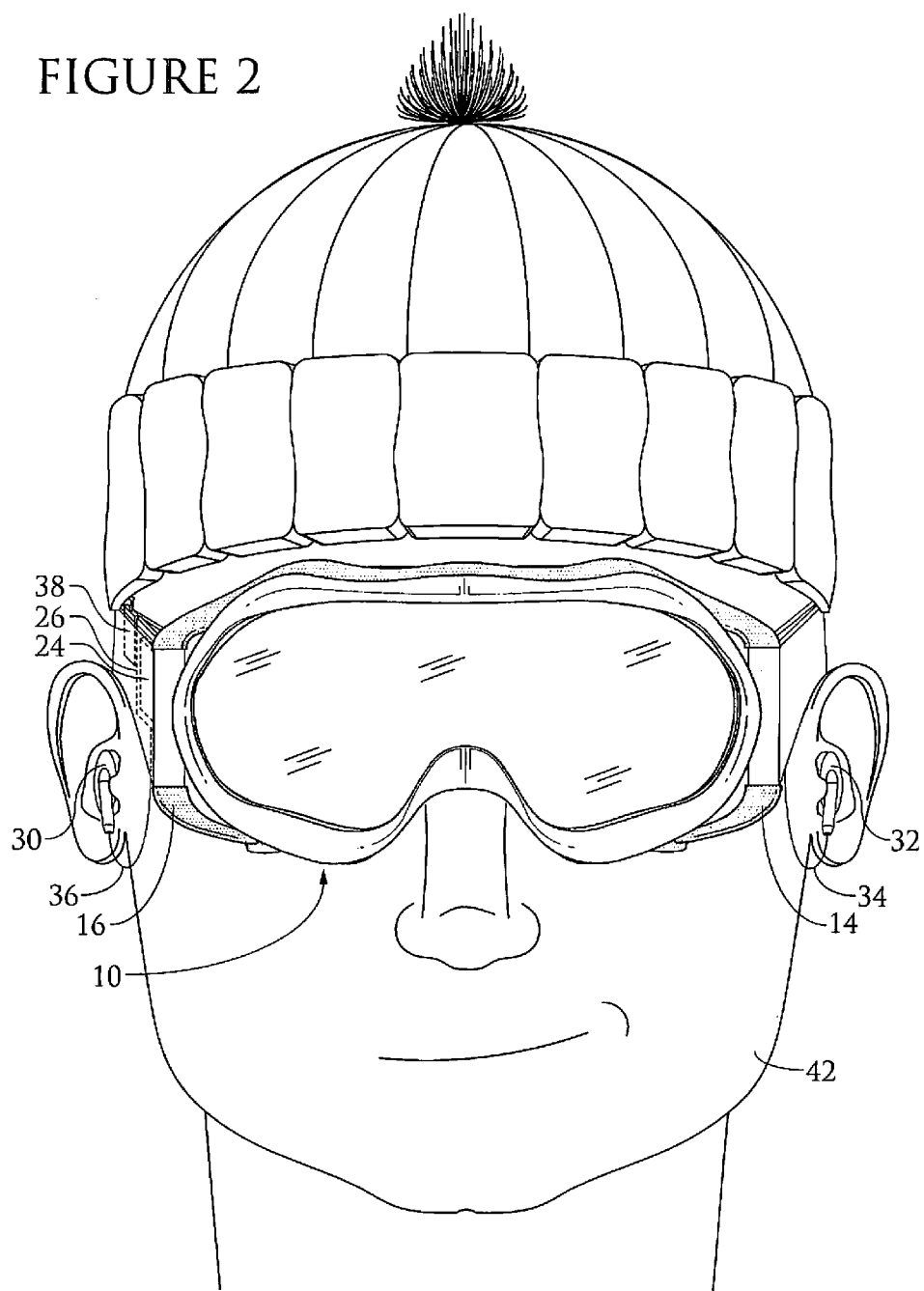
FIG. 2 shows a face of a skier wearing the ski goggles with digital player and transmitter embodiment

FIG. 1 shows a ski goggle (10) having a face plate (12), a first side connector (14), and a second side connector (16) each having an adjustment device (18) and (20) to shorten or lengthen a strap (22) which goes around the head of a user (shown in FIG. 2).

A digital player (24) is secured in a housing (26) which is fastened, such as with locking fasteners (28), such as screws or alternatively a C-Clip (no shown) to one of the two connectors. The digital player can be a mini IPOD™, such as those sold by Apple computer company of California. The mini IPOD™ is a compact digital player which connects to a computer to download digital music files, and the player is battery operated with an integrated battery that is rechargeable. Alternatively, an MP3 player or a miniature radio can be used. The housing can be made of plastic, Velcro™ woven fabric, or elastic material.

The miniature digital player (24) connects to earphones (30) and (32) using a first wire (34) that goes from the digital player (24) across the faceplate (12) at the upper most portion to the connector (14) and then to the earphone (32) and a second wire (36) that goes from the digital player (24) to the connector (16) and then down to the earphone (30). Additionally, the miniature digital player (24) can be engaged with a mini-transmitter/receiver (38) removeably connected to the housing (26) and engaging the digital player with a wired connection (40). The mini-transmitter and receiver (38) is preferably an El-Pro wireless transmitter/receiver available from Elextromax of Houston Tex. This unit is small, and transmits over 2000 feet, which is the length of the typical mogul race course and has its own battery.

Audience members can wear receiver units to hear the transmissions from the digital player on the skier without the need to broadcast the loud music over the slopes causing crashes on adjacent slopes by kids cutting off skiers as they go to view the racers because of the loud music, and it is really loud. It is contemplated that the mini wireless transmitter/receiver can be a cell phone transmitting over a cell network.

FIG. 2 shows and embodiment of the digital player (28) in the housing (26) on the ski goggles (10) transmitter/receiver on the head of a user (42) with an earphone in each ear (46) and (48) respectively. This embodiment lets the skier practice the race runs with the digital music player, so that only the racer or the skier hears the music.

Figure 3:
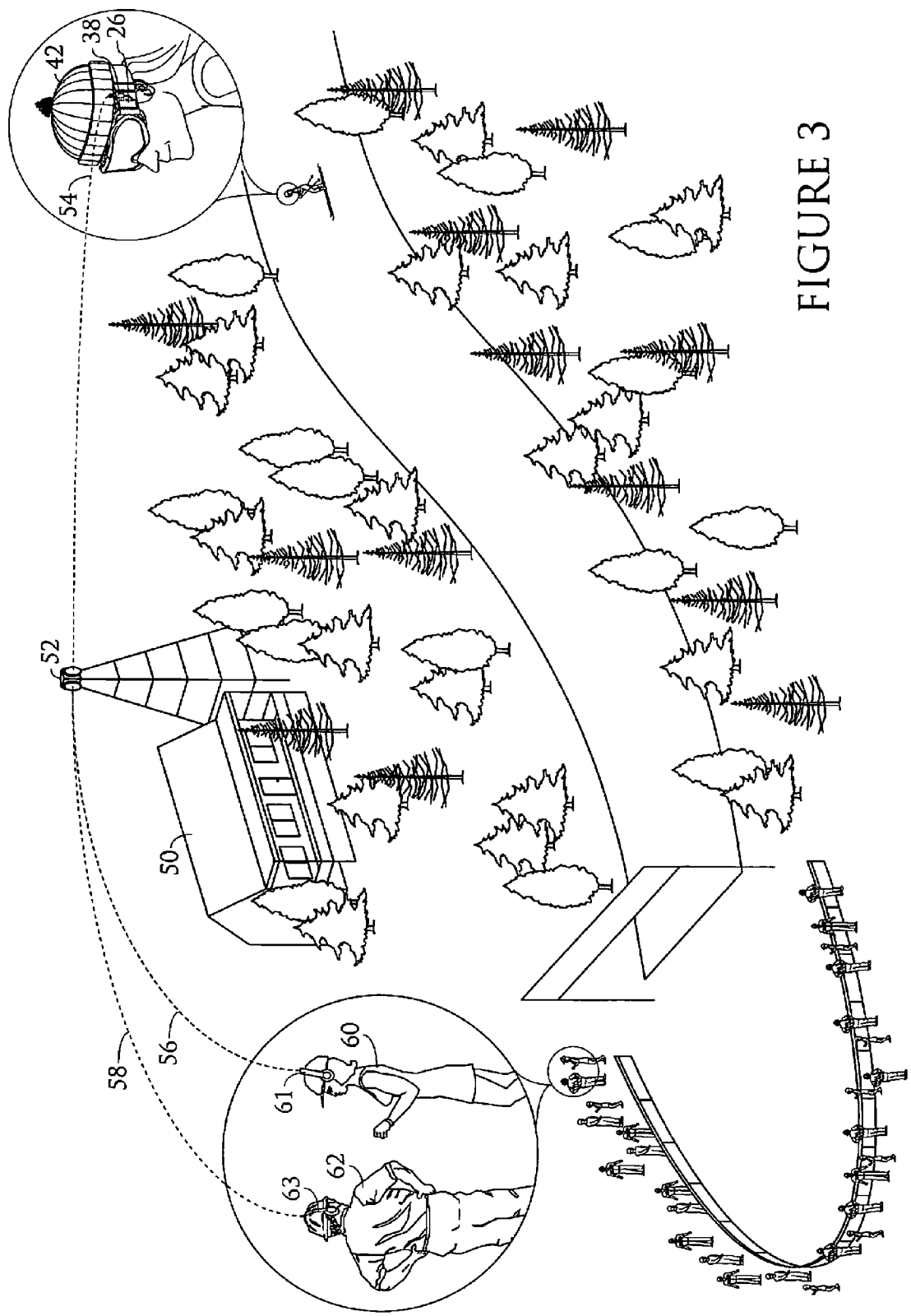
FIG. 3 depicts a race slope with the racer wearing the ski goggle of FIG. 1 and audience members wearing synched receivers and the transmitter of the digital music file over a wireless connection.

FIG. 3 shows the user (42) wearing the ski goggles with digital player and transmitter of FIG. 1 going down a ski slope broadcasting to a base station (50) having a repeater (52) for conveying the signal (54) from the user (42) to a first audience member (60) wearing receiving headphones (61) and a second audience member (62) wearing headphones (63) using a first repeater signal (56) and a second repeater signal (58). It is also contemplated that the user (42) could be able to transmit within range of the first and second audience members without a repeater unit (52), which are commonly available, particularly if the embodiment is a cellular connection. The headphones wearable by the audience members can be Zen-sonic Wireless Headphones from Morely, Australia with the repeater available from the same company.

It is contemplated that the first and second earphone in another embodiment can be in wireless communication with the miniature digital player.

It is important to the quality of the sound for practice and for use on television, as most of these races are televised that digital music and a digital music player be used, particularly since the cable channels are developing high definition images, they need high definition sound to go with it. The cable stations will not accept fuzzy music from the skier, and this invention enables the digital music to be broadcast directly from the user to the television receiver at the base of the ski slope for very high quality sound which was not previously available.

Use of the digital players with numerous skiers will generate a very high quality sound and image picture, which can be copied more easier and used to education and practice Olympic skiers with greater detail than every before.

In the use of the invention, this device will stop the crashes that occur on the adjacent ski slopes during races, which for people over 40, would be really important and add a significant safety element to skiing not available before this invention.

The invention also contemplates a ski area having a ski slope with controlled music transmission that is not broadcast through loudspeakers, but only played through the unique ski goggles with digital player described herein. The ski area would have a ski slope, one or more of them with repeater units placed alongside the slope. A transmitter would be in communication with the repeater units. The ski area could play music on different slopes, rock and roll on one slope, jazz on another, new age on another and skiers would hear the different types of music, like music at a theme part by skiing with ski goggles that received the digital transmissions. It would be a new kind of entertainment for a ski area which would involve a premium paid by the skiers to rent or lease the units from the ski area to obtain the "total sensory" experience with the skiing. These ski goggles could have digital music receivers and earphones for receiving transmitted digital music; the repeater units placed on each slope for providing digital music transmissions without loudspeakers; and a transmitter for broadcasting the digital music on a frequency without the use of speakers in communication with the repeater units; digital music files available for transmission by the transmitter.

The invention contemplates a skiing theme park which has different music transmitted silently, so as not to bother other skiers, along each slope, rock and roll on the moguls, and cool jazz on the blue runs for an easy slide, for which skiers would pay a premium for the unique total sensory experience. More specifically, some of the different styles of music could be rock and roll, jazz, classical, new age, country, rap, top 40, big band, oldies, and combinations thereof.

While these embodiments have been described with emphasis on the preferred embodiments, it should be understood that within the scope of the appended claims, the embodiments might be practiced other than as specifically described herein.

What is claimed is:

1. A ski theme park comprising: (a) ski slopes with specially designed digital music tracks for each slope; (b) ski goggles with digital music receivers and earphones for skiers to wear and receive the specially designed digital music tracks on a slope by slope basis; (c) repeater units placed on each slope for providing the specially designed digital music tracks for each slope without loudspeakers; (d) at least one transmitter for broadcasting the specially designed digital music to each slope on a frequency only received by the ski goggles and without the use of speakers along the slope, and wherein the transmitter is in communication with the repeater units; and (e) digital music files available for transmission by the transmitter.

2. The ski theme park of claim 1, wherein the specially designed digital music comprises a different style of music for individual slopes.

3. The ski theme park of claim 2, wherein the different style of music is selected from the group: rock and roll, jazz, classical, new age, country, rap, top 40, big band, oldies, and combinations thereof.

* * * * *